(12) United States Patent
Epshtein

(10) Patent No.: US 9,945,868 B2
(45) Date of Patent: *Apr. 17, 2018

(54) METHOD FOR DETERMINING DEGREE OF MODIFIED POTENCY OF BIPATHIC MEDICAMENT

(71) Applicant: Oleg Iliich Epshtein, Moscow (RU)

(72) Inventor: Oleg Iliich Epshtein, Moscow (RU)

(73) Assignee: Oleg Illich Epshtein, Moscow (RU)

( * ) Notice: Subject to any disclaimer, the term of this patent is extended or adjusted under 35 U.S.C. 154(b) by 0 days.

This patent is subject to a terminal disclaimer.

(21) Appl. No.: 14/218,081

(22) Filed: Mar. 18, 2014

(65) Prior Publication Data

US 2014/0287442 A1    Sep. 25, 2014

(30) Foreign Application Priority Data

Mar. 18, 2013  (RU) ................. 2013111961

(51) Int. Cl.
| | | |
|---|---|---|
| *G01N 30/00* | (2006.01) | |
| *G01N 33/68* | (2006.01) | |
| *G01N 24/08* | (2006.01) | |
| *G06F 19/00* | (2018.01) | |

(52) U.S. Cl.
CPC ....... *G01N 33/6854* (2013.01); *G01N 24/088* (2013.01); *G01N 30/00* (2013.01); *G06F 19/702* (2013.01)

(58) Field of Classification Search
USPC ......... 435/25; 436/547; 424/158.1; 324/309; 702/22
See application file for complete search history.

(56) References Cited

U.S. PATENT DOCUMENTS

| | | |
|---|---|---|
| 7,572,441 B2 | 8/2009 | Epshtein et al. |
| 7,582,294 B2 | 9/2009 | Epshtein et al. |
| 7,700,096 B2 | 4/2010 | Epshtein et al. |
| 7,815,904 B2 | 10/2010 | Epshtein et al. |
| 7,923,009 B2 | 4/2011 | Epshtein et al. |
| 8,066,992 B2 | 11/2011 | Epshtein |
| 8,168,182 B2 | 5/2012 | Epshtein |
| 8,178,498 B1 | 5/2012 | Epshtein |
| 8,241,625 B2 | 8/2012 | Epshtein et al. |
| 8,524,229 B2 | 9/2013 | Epshtein et al. |
| 8,535,664 B2 | 9/2013 | Epshtein et al. |
| 8,617,555 B2 | 12/2013 | Epshtein |
| 8,637,030 B2 | 1/2014 | Epshtein |
| 8,637,034 B2 | 1/2014 | Epshtein |
| 8,703,124 B2 | 4/2014 | Epshtein et al. |
| 8,795,657 B2 | 8/2014 | Epshtein |
| 8,815,245 B2 | 8/2014 | Epshtein |
| 2006/0153845 A1 | 7/2006 | Epshtein et al. |
| 2007/0123518 A1 | 5/2007 | Epshtein |
| 2007/0141058 A1 | 6/2007 | Epshtein et al. |
| 2008/0025985 A1 | 1/2008 | Epshtein et al. |
| 2008/0050360 A1 | 2/2008 | Epshtein et al. |
| 2008/0050392 A1 | 2/2008 | Epshtein et al. |
| 2008/0131440 A1 | 6/2008 | Epshtein et al. |
| 2009/0148521 A1 | 6/2009 | Epshtein |
| 2010/0166762 A1 | 7/2010 | Epshtein |
| 2010/0203059 A1 | 8/2010 | Epshtein |
| 2010/0221258 A1 | 9/2010 | Epshtein |
| 2010/0239569 A1 | 9/2010 | Epshtein |
| 2011/0008452 A1 | 1/2011 | Epshtein et al. |
| 2011/0086037 A1 | 4/2011 | Epshtein |
| 2012/0225074 A1 | 9/2012 | Epshtein et al. |
| 2012/0258146 A1 | 10/2012 | Epshtein |

(Continued)

FOREIGN PATENT DOCUMENTS

| | | |
|---|---|---|
| EP | 2123300 A1 | 11/2009 |
| RU | 2112976 C1 | 6/1998 |

(Continued)

OTHER PUBLICATIONS

Frimel G., "Immunological Methods", 1987, Moscow, Medicina Publishing House, pp. 9-33.
Schwabe, W., "German Homeopathic Pharmacopia (Homoepathisches Arznibuch)," Stuttgart, Translatiaon of the 5th Supplement (1991) to the 1978 edition.
Grimm, et al., "Review of Electro-Assisted Methods for Water Purification," Desalination, 1998, vol. 115, pp. 285-294.
Labconco Corporation, "A Guide to Laboratory Water Purification," 2003.
Koznacheev I.A., et al., "Water Purification of Organic Inclusions in a Reverse Flow Filtration Combustion Reactor," International Journal of Heat and Mass Transfer, 2011, vol. 54, pp. 932-937.
Laffly, et al., "Monoclonal and Recombinant Antibodies, 30 Years After . . . " Human Antibodies, 2005, vol. 14, pp. 33-55.

(Continued)

*Primary Examiner* — Ralph J Gitomer
(74) *Attorney, Agent, or Firm* — Pergament & Cepeda LLP; Milagros A. Cepeda; Edward D. Pergament

(57) ABSTRACT

The invention comprises a method for determining degree of modified potency of a bipathic medicament. A bipathic medicine is a medicament comprising a therapeutic component and a homeopathic component, wherein the homeopathic component has some physical, chemical or biological affect on the therapeutic component and/or the pharmacological efficacy thereof. An analytical measurement of at least one characteristic parameter of the therapeutic form is made prior to its interaction with the activated-potentiated form. The same analytical measurement(s) are made and after interaction between the therapeutic and activated-potentiated forms. This data is used to confirm the presence of any modified potency is caused by the presence of molecular form in the activated-potentiated form. Further, the claimed analytical measurement of at least one characteristic parameter of the therapeutic form prior to its interaction with the activated-potentiated form and again after such interaction serves to quantify the degree of modifying potency associated with the activated-potentiated form in relative dimensionless activity units (release activity).

8 Claims, 1 Drawing Sheet

(56) References Cited

U.S. PATENT DOCUMENTS

| | | |
|---|---|---|
| 2012/0263725 A1 | 10/2012 | Epshtein et al. |
| 2012/0263726 A1 | 10/2012 | Epshtein et al. |
| 2012/0294899 A1 | 11/2012 | Epshtein et al. |
| 2012/0321672 A1 | 12/2012 | Epshtein |
| 2013/0017202 A1* | 1/2013 | Epshtein et al. ........... 424/139.1 |
| 2013/0045237 A1 | 2/2013 | Epshtein et al. |
| 2013/0058981 A1 | 3/2013 | Epshtein |
| 2013/0058982 A1 | 3/2013 | Epshtein |
| 2013/0064860 A1 | 3/2013 | Epshtein |
| 2013/0171161 A1 | 7/2013 | Epshtein et al. |
| 2013/0189707 A1 | 7/2013 | Epshtein et al. |
| 2013/0224219 A1 | 8/2013 | Epshtein et al. |
| 2013/0302312 A1 | 11/2013 | Epshtein et al. |
| 2013/0303735 A1 | 11/2013 | Epshtein et al. |
| 2013/0315964 A1 | 11/2013 | Epshtein et al. |
| 2013/0336985 A1 | 12/2013 | Epshtein et al. |
| 2014/0010819 A1 | 1/2014 | Epshtein et al. |
| 2014/0056923 A9 | 2/2014 | Epshtein et al. |
| 2014/0079696 A1* | 3/2014 | Epshtein ................ 424/134.1 |
| 2014/0112934 A1 | 4/2014 | Epshtein |
| 2014/0287442 A1* | 9/2014 | Epshtein ................. 435/7.92 |

FOREIGN PATENT DOCUMENTS

| | | |
|---|---|---|
| RU | 2161955 C1 | 1/2001 |
| RU | 2181890 C1 | 4/2002 |
| RU | 2191601 C1 | 10/2002 |
| RU | 2192888 C1 | 11/2002 |
| RU | 2195648 * | 12/2002 |
| RU | 2195648 C2 | 12/2002 |
| RU | 2438707 C2 | 1/2007 |
| RU | 2332236 C1 | 8/2008 |

OTHER PUBLICATIONS

Stewart, "The Production of High-Purity Water in the Clinical Laboratory," Laboratory Medicine, Nov. 2000, vol. 31, No. 11, pp. 605-611.

Notification of Transmittal of the International Search Report and the Written Opinion of the International Searching Authority, dated Oct. 13, 2014, for corresponding International Patent Application No. PCT/IB2014/001267.

International Search Report, dated Oct. 13, 2014, for corresponding International Patent Application No. PCT/IB2014/001267.

Written Opinion of the International Searching Authority, dated Oct. 13, 2014, for corresponding International Patent Application No. PCT/IB2014/001267.

Pavlov, I.F., et al., "Morphine and Antibodies to u-Opiate Receptors in Ultralow Doses: Effect on Oxygen Consumption," Bull Exp Biol Med, 2003, Suppl. 1, pp. 137-139.

Epshtein O.I., et al., "In Vitro Effects of Bipathic Treatment with Antibodies in Ultralow Doses during Long-Term Post-Tetanic Potentiation," Bull Exp Biol Med., 2003, Suppl. 1, pp. 111-113.

Voronina T.A., et al., "Study of Bipathic Effect of Haloperidol," Bull Exp Biol Med., 2008, vol. 145, No. 5, pp. 620-622.

* cited by examiner

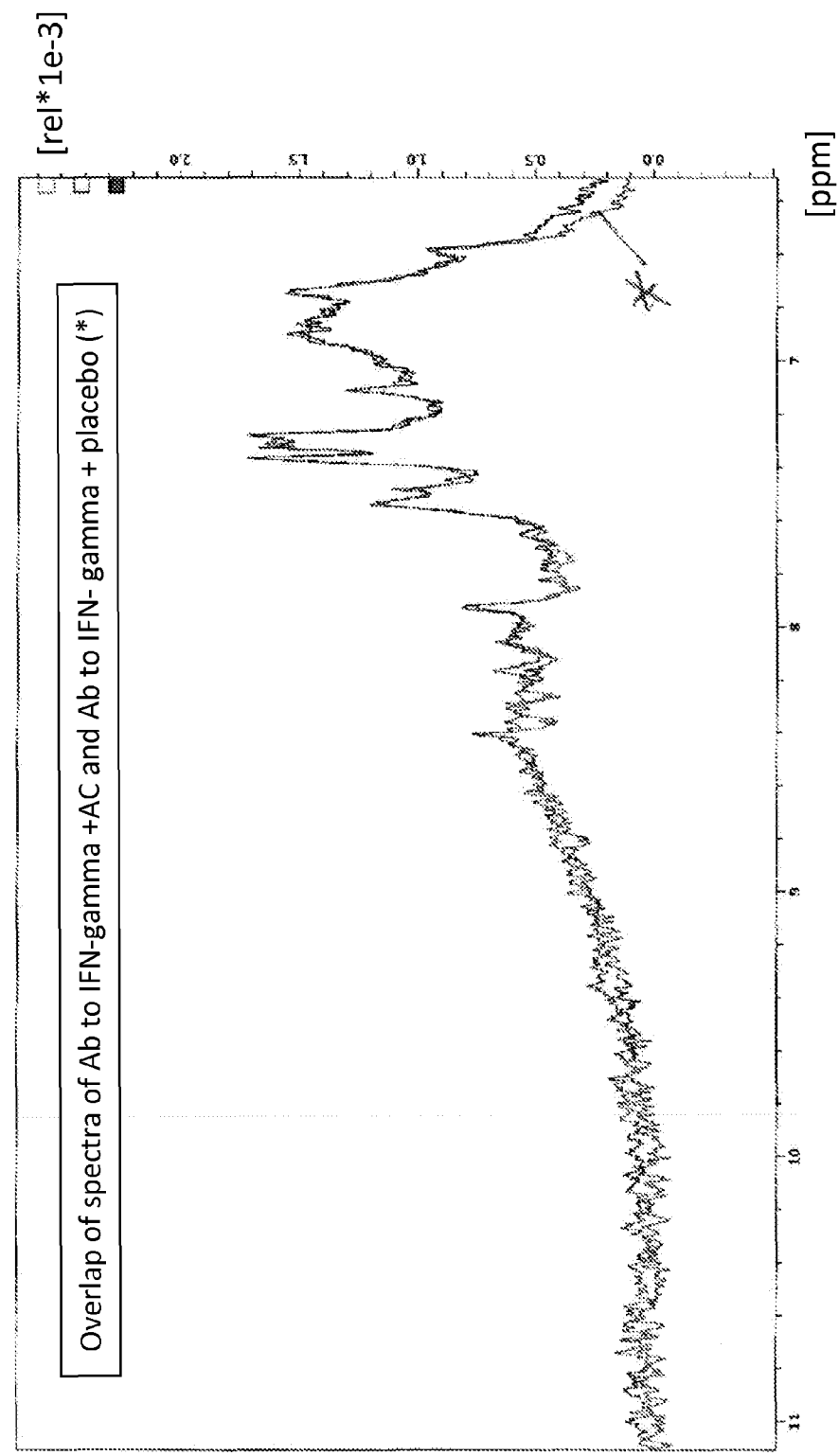

METHOD FOR DETERMINING DEGREE OF MODIFIED POTENCY OF BIPATHIC MEDICAMENT

This application claims priority to Russian patent application No. 2013111961 filed on Mar. 18, 2013, which is hereby incorporated by reference in its entirety.

FIELD

The invention relates to the field of medicine, specifically pharmaceuticals. The invention is used for determining the modified potency of drugs, especially bipathic drugs at least one component of which is prepared according to homeopathic techniques, in a reliable and reproducible manner.

BACKGROUND

Activated-Potentiated Form

Medicaments prepared according to homeopathic techniques include those prepared by homeopathic potentiation, also referred to as activation, through multiple consecutive dilutions in a carrier (water or water-alcohol solvent)—thereby decreasing concentration—in combination with shaking of each consecutive dilution. See, e.g., RU 2191601 C1; RU 2192888 C1; RU 2332236 C1 (English version found at EP 2 123 300); and RU 2438707 C2 (U.S. Pat. Pub. 2011/0008452). The result of preparation by homeopathic potentiation is a medicament which contains low or ultra-low doses of initial medicament; dilution may proceed to approximate or exceed 1 mole of carrier per molecule of the initial medicament in molecular form, keeping in mind the total number of molecules per mole is given by Avogadro's number ($6.022 \times 10^{23}$ mol$^{-1}$). The term molecular form is further defined below. In the context of a solid, dilution is referred to as trituration. Through homeopathic techniques the carrier may acquire modifying potency, manifested in its ability to alter physical, chemical and/or biological properties of the starting substance when treated by the said activated-potentiated form (RU 2161955 C1).

The term "molecular form" is used to denote one or more molecules of a particular chemical substance. Thus, the molecular form of aspirin can be a single molecule of acetylsalicylic acid; 1 mole of aspirin in molecular form consists of $6.022 \times 10^{23}$ molecules of acetylsalicylic acid and weighs 180.157 grams.

The term "activated-potentiated form" is used to denote a product of homeopathic potentization of an initial solution containing a molecular form of a substance. In other words, a solution containing the molecular form of a substance, e.g., a specific antibody or organic molecule, is subjected to repeated consecutive dilution and multiple vertical shaking of each obtained solution in accordance with homeopathic techniques. The preferred diluent, often called the carrier, is water or a water-ethyl alcohol mixture. The preferred concentration of the molecular form in the initial carrier ranges from about 0.5 to about 5.0 mg/ml. The activated-potentiated form may be prepared from an initial solution by homeopathic potentization, preferably using the method of proportional concentration decrease by serial dilution of 1 part of each preceding solution. Thus, 1 part of the initial solution is mixed with 99 parts (for centesimal dilution) of the carrier and subjected to external impact. Preferably, the external impact involves multiple vertical shaking (dynamization) of each dilution. This results in the creation of the 1st centesimal dilution, denoted C1. The 2nd centesimal dilution (C2) is prepared by mixing 1 part of the 1st centesimal dilution C1 with 99 parts of the carrier. This procedure is repeated 10 additional times to prepare the 12th centesimal dilution C12. Separate containers are typically used for each subsequent dilution up to the required dilution factor. Similar procedures with the relevant dilution factor are performed to obtain, for example, dilutions C30, C50 and C200. This method is well-accepted in the homeopathic art. See, e.g. V. Schwabe "Homeopathic medicines", M., 1967, p. 14-29, incorporated herein by reference for the purpose stated. C12, C30, and C200 represent dilutions of the primary matrix solution (mother tincture) of antibodies $100^{12}$, $100^{30}$ and $100^{200}$ times, respectively.

Preferred activated-potentiated forms are often a mixture of several centesimal dilutions of the same molecular form. For example, a mixture of C12, C30, and C50 dilutions or C12, C30 and C200 dilutions. When using the mixture of various homeopathic dilutions each component of the composition, e.g., C12, C30, C50, C200, is prepared separately according to the above-described procedure until the next-to-last dilution is obtained, i.e., until C11, C29, and C199 respectively, and then one part of each component is added in one container according to the mixture composition and mixed with the required quantity of the carrier, i.e., 97 parts for centesimal dilution.

Examples of homeopathic potentization are described in U.S. Pat. Nos. 7,572,441 and 7,582,294, which are incorporated herein by reference in their entirety and for the purpose stated. The term "activated-potentiated form" and the term "ultra-low doses" are meant as fully supportive and primarily synonymous with one another.

Homeopathic Bipathy

U.S. Pat. No. 8,178,498 describes the concept of bipathic medicinal forms. Bipathic medicinal preparations combine therapeutic values of a medicinal substance in therapeutic dose and an activiated-potentiated preparation chemically homogeneous with the medicinal substance but different in mechanism of action on the organism. Put another way, the described bipathic medicinal preparation combines the molecular form of a medicinal substance in approximately its standard concentration and an activiated-potentiated form derived from the same molecular form but having its molecular form present, if at all, in ultra-low concentration. The standard dose and activated-potentiated form, either combined or administered approximately simultaneously, are shown to promote biological activation and induce positive morphological and functional changes in the form of "systemic adaptation" responsible for increased therapeutic efficiency of the active medicinal substance with reduced risk of patients' individual reactions and undesirable adverse side-effects or after-effects.

Moreover, "bipathic" simultaneous administration of medicinal substance in therapeutic dose and activated-potentiated form, according to U.S. Pat. No. 8,178,498: (1) allows for lower conventional doses of the substance, (2) prevents habituation due to enzyme "induction", and (3) prevents overdosage owing to neutralization of negative energies and stimulation of certain organs and of the whole. U.S. Pat. No. 8,178,498 is incorporated herein by reference in its entirety and for the purpose stated.

Qualitative/Quantitative Assessment of Medicaments

Known in the art, e.g., RU 2181890 C1, is a method to determine the biological activity of a substance. The activity is represented by a ratio between the rate of enzymatic response to a test sample before and after adding a substance. An "optimal substance concentration in a sample" is determined in vitro. This method is not suitable, however, for determining the potency of medicaments prepared according to homeopathic techniques.

Known in the art is the method of determining homeopathic medicament potency by applying linearly polarized coherent optical radiation to an activated medicament present in a constant magnetic field. Scattered transmitted radiation is measured using time-related accumulation of values of its polarized component intensity in the mode of optical bias from different points of test medium. Analysis is conducted to calculate frequency spectrum of ultra low fluctuations of transmitted intensity and data is compared with a standard specimen. See, e.g., RU 2112976 C1.

Also known is the method for qualitative determination of homeopathic medicine or activated-potentiated form. The method includes treating a test medium with a standard specimen and registration of alterations of physical and chemical parameters. A set of known substances are used which structure and/or composition are approximately similar or similar to the ones of the determined homeopathic medicine or to the ones of potentiated substance form as well as structure and/or composition of antibodies to these known substances. Identification of homeopathic medicine or potentiated substance form shall be based on the known substance, which reaction with the appropriate antibody when homeopathic medicine or potentiated substance form are introduced into reaction medium is accompanied by alterations registered using immunochemical analytical methods based on antigen-antibody reaction (RU 2195648 C2).

The prior art methods do not, however, provide reliable and reproducible qualitative and quantitative determination of drug identity and potency associated with an activated-potentiated form. This includes activated medicaments prepared according to homeopathic techniques described above.

SUMMARY OF THE INVENTION

A method of determining activity of activated-potentiated form of a substance, said method comprising: providing an activated-potentiated form of a substance, assuring absence of molecular form of the substance in said activated-potentiated form, providing a molecular form of said substance, measuring at least one physical, chemical or biological parameter (A) of said molecular form of said substance using a suitable analytical method, treating said molecular form of said substance with said activated-potentiated form of said substance, and measuring said at least one physical, chemical or biological parameter (Am) of said treated molecular form of said substance using said analytical method, wherein said activity of said activated-potentiated form of said substance is the degree of difference between A and Am.

The method described above, further comprising expressing said activity of said activated-potentiated form of said substance in relative units (X) in accordance with the formula $X = C|A - A_M|/A$.

The method described above, further comprising i) treating a molecular form of a different substance with said activated-potentiated form of the first substance, ii) measuring said at least one physical, chemical or biological parameter (B) of said molecular form of said different substance said analytical method, iii) measuring said at least one physical, chemical or biological parameter ($B_M$) of said treated molecular form of said different substance using said analytical method to determine specificity of said method, wherein said method is considered specific when said at least one physical, chemical or biological parameter changes in statistically significant manner for $A - A_M$ and does not change in statistically significant manner for $B - B_M$.

The method described above, wherein said analytical method is High Performance Liquid Chromatography.

The method described above, wherein said analytical method is enzyme immune assay analysis.

The method described above, wherein said analytical method is Nuclear Magnetic Resonance.

The method described above, wherein said step of assuring absence of molecular form of the substance comprises removing the molecular form of said substance.

The method described above, wherein said substance is an antibody.

The method described above, wherein said antibody is a polyclonal antibody.

The method described above, wherein said substance is a small organic molecule.

The method described above, wherein said activated-potentiated form is a liquid.

The method described above, wherein said activated-potentiated form is impregnated onto a solid carrier.

BRIEF DESCRIPTION OF THE FIGURES

FIG. 1 shows overlap of NMR spectra of Ab to IFN-gamma+AC and Ab to IFN-gamma+purified water.

DETAILED DESCRIPTION OF THE INVENTION

The invention is defined with reference to the appended claims. With respect to the claims, relevant definitions have been provided above and additional definitions are provided herein.

The term "antibody" as used herein shall mean an immunoglobulin that specifically binds to, and is thereby defined as complementary with, a particular spatial and polar organization of another molecule. Antibodies as recited in the claims may include a complete immunoglobulin or fragment thereof, may be natural, polyclonal or monoclonal, and may include various classes and isotypes, such as IgA, IgD, IgE, IgG1, IgG2a, IgG2b and IgG3, IgM, etc. Fragments thereof may include Fab, Fv and F(ab')$_2$, Fab', and the like. The singular "antibody" includes plural "antibodies."

The terms "activated-potentiated form" or "potentiated form" are used to denote a product of homeopathic potentization of any initial solution containing a molecular form of a substance, e.g., an antibody. Examples of homeopathic potentization of antibodies are described in U.S. Pat. Nos. 7,572,441 and 7,582,294, which are incorporated herein by reference in their entirety and for the purpose stated. An antibody is in the "activated-potentiated" or "potentiated" form when three factors are present. First, the "activated-potentiated" form of the antibody is a product of a preparation process well accepted in the homeopathic art. Second, the "activated-potentiated" form of antibody must have biological activity determined by methods well accepted in modern pharmacology. Third, the biological activity exhibited by the "activated-potentiated" form of the antibody cannot be explained by the presence of the molecular form of the antibody in the final product of the homeopathic process.

There has been a considerable amount of controversy regarding homeopathic treatment of human subjects. While the present invention relies on accepted homeopathic processes to obtain the "activated-potentiated" form of a substance, i.e., molecular form, it does not rely solely on homeopathy in human subjects for evidence of activity. Particular to molecular forms consisting of antibodies, it has been surprisingly discovered by the inventor of the present application and amply demonstrated in the accepted pharmacological models that the solvent ultimately obtained from consecutive multiple dilution of a starting molecular form of an antibody has definitive activity unrelated to the presence of the traces of the molecular form of the antibody in the target dilution. Also, the claimed "activated-potentiated" form of antibody encompasses only solutions or solid preparations the biological activity of which cannot be explained by the presence of the molecular form of the antibody remaining from the initial, starting solution. In other words, while it is contemplated that the "activated-potentiated" form of the antibody may contain traces of the initial molecular form of the antibody, one skilled in the art could not attribute the observed biological activity in the accepted pharmacological models to the remaining molecular form of the antibody with any degree of plausibility due to the extremely low concentrations of the molecular form of the antibody remaining after the consecutive dilutions. While the invention is not limited by any specific theory, the biological activity of the "activated-potentiated' form of the antibodies of the present invention is not attributable to the initial molecular form of the antibody. Preferred is the "activated-potentiated" form of antibody in liquid or solid carrier in which the concentration of the molecular form of the antibody is below the limit of detection of the accepted analytical techniques, such as capillary electrophoresis and High Performance Liquid Chromatography. Particularly preferred is the "activated-potentiated" form of antibody in liquid or solid form in which the concentration of the molecular form of the antibody is below the Avogadro number, i.e., 1 molecule of molecular form per $6.022 \times 10^{23}$ molecules of carrier.

The pharmaceutical composition of the invention expands the arsenal of preparations available for the treatment prophylaxis of the infectious diseases, including bacterial infections and acute and chronic viral infections.

The combination pharmaceutical composition in accordance with this aspect of the invention may be in the liquid form or in solid form. The preferred procedure for preparing the activated-potentiated component of the combination drug according to the present invention is the use of the mixture of three aqueous-alcohol dilutions of the primary matrix solution of antibodies diluted $100^{12}$, $100^{30}$ and $100^{50}$ times, respectively, which is equivalent to centesimal homeopathic dilutions C12, C30, and C50 or diluted $100^{12}$, $100^{30}$ and $100^{200}$ times, respectively, which is equivalent to centesimal homeopathic dilutions C12, C30 and C200. To prepare a solid dosage form, a solid carrier is treated with the desired dilution obtained via the homeopathic process. To obtain a solid unit dosage form of the combination of the invention, the carrier mass is impregnated with each of the dilutions. Both orders of impregnation are suitable to prepare the desired combination dosage form.

In the event that the activated-potentiated form included in the pharmaceutical composition is prepared from an initial molecular form of the antibody, it is done so in a process accepted in homeopathic art. The starting antibodies may be monoclonal, or polyclonal antibodies prepared in accordance with known processes, for example, as described in Immunotechniques, G. Frimel, M., "Meditsyna", 1987, p. 9-33; "Hum. Antibodies. Monoclonal and recombinant antibodies, 30 years after" by Laffly E., Sodoyer R.-2005-Vol. 14.-N 1-2. P. 33-55, both incorporated herein by reference.

Monoclonal antibodies may be obtained, e.g., by means of hybridoma technology. The initial stage of the process includes immunization based on the principles already developed in the course of polyclonal antisera preparation. Further stages of work involve the production of hybrid cells generating clones of antibodies with identical specificity. Their separate isolation is performed using the same methods as in the case of polyclonal antisera preparation.

Polyclonal antibodies may be obtained via active immunization of animals. For this purpose, for example, suitable animals (e.g. rabbits) receive a series of injections of the appropriate antigen (cytokine and receptor). The animals' immune system generates corresponding antibodies, which are collected from the animals in a known manner. This procedure enables preparation of a monospecific antibody-rich serum.

If desired, the serum containing antibodies may be purified, for example by using affine chromatography, fractionation by salt precipitation, or ion-exchange chromatography. The resulting purified, antibody-enriched serum may be used as a starting material for the preparation of the activated-potentiated form of the antibodies. The preferred concentration of the resulting initial solution of antibody in the solvent, preferably water or a water-ethyl alcohol mixture, ranges from about 0.5 to about 5.0 mg/ml.

An exemplary procedure for preparation of a molecular form consisting of polyclonal antibodies to CD4 receptor may be described as follows. In 7-9 days before blood sampling, 1-3 intravenous injections of the desired antigen are made to the rabbits to increase the level of polyclonal antibodies in the rabbit blood stream. Upon immunization, blood samples are taken to test the antibody level. Typically, the maximum level of immune reaction of the soluble antigen is achieved within 40 to 60 days after the first injection of the antigen. Upon completion of the first immunization cycle, rabbits have a 30-day rehabilitation period, after which re-immunization is performed with another 1-3 intravenous injections. To obtain antiserum containing the desired antibodies, the immunized rabbits' blood is collected from rabbits and placed in a 50 ml centrifuge tube. Product clots formed on the tube sides are removed with a wooden spatula, and a rod is placed into the clot in the tube center. The blood is then placed in a refrigerator for one night at the temperature of about 40° C. On the following day, the clot on the spatula is removed, and the remaining liquid is centrifuged for 10 min at 13,000 rotations per minute. Supernatant fluid is the target antiserum. The obtained antiserum is typically yellow. 20% of NaN3 (weight concentration) is added in the antiserum to a final concentration of 0.02% and stored before use in frozen state at the temperature of −20° C. or without NaN3 at the temperature of −70° C. To separate the target antibodies to gamma interferon from the antiserum, the following solid phase absorption sequence is suitable:

10 ml of the antiserum of rabbits is diluted twofold with 0.15 M NaCl, after which 6.26 g Na2SO4 is added, mixed and incubated for 12-16 hours at 4° C. The sediment is removed by centrifugation, diluted in 10 ml of phosphate buffer and dialyzed against the same buffer during one night at ambient temperature. After the sediment is removed, the solution is applied to a DEAE-cellulose column balanced by phosphate buffer. The antibody fraction is determined by measuring the optical density of the eluate at 280 nm.

The isolated crude antibodies are purified using affine chromatography method by attaching the obtained antibodies to CD4 antigen located on the insoluble matrix of the chromatography media, with subsequent elution by concentrated aqueous salt solutions.

The resulting buffer solution is used as the initial solution for the homeopathic dilution process used to prepare the activated-potentiated form of the antibodies. The preferred concentration of the initial matrix solution of the antigen-purified polyclonal rabbit antibodies to CD4 receptor is 0.5 to 5.0 mg/ml, preferably, 2.0 to 3.0 mg/ml.

Preferably, the pharmaceutical composition in the solid unit dosage form is prepared from granules of the pharmaceutically acceptable carrier which was previously saturated with the aqueous or aqueous-alcoholic dilutions of the activated-potentiated form of antibodies CD4 receptor. The solid dosage form may be in any form known in the pharmaceutical art, including a tablet, a capsule, a lozenge, and others. As an inactive pharmaceutical ingredients one can use glucose, sucrose, maltose, amylum, isomaltose, isomalt and other mono-, oligo- and polysaccharides used in manufacturing of pharmaceuticals as well as technological mixtures of the above mentioned inactive pharmaceutical ingredients with other pharmaceutically acceptable excipients, for example isomalt, crospovidone, sodium cyclamate, sodium saccharine, anhydrous citric acid etc.), including lubricants, disintegrants, binders and coloring agents. The preferred carriers are lactose and isomalt. The pharmaceutical dosage form may further include standard pharmaceutical excipients, for example, microcrystalline cellulose, magnesium stearate and citric acid.

To prepare the solid oral form, 100-300 μm granules of lactose are impregnated with aqueous or aqueous-alcoholic solutions of the activated-potentiated form of antibodies to CD4 receptor in the ratio of 1 kg of antibody solution to 5 or 10 kg of lactose (1:5 to 1:10). To effect impregnation, the lactose granules are exposed to saturation irrigation in the fluidized boiling bed in a boiling bed plant (e.g. "Hüttlin Pilotlab" by Hüttlin GmbH) with subsequent drying via heated air flow at a temperature below 40° C. The estimated quantity of the dried granules (10 to 34 weight parts) saturated with the activated-potentiated form of antibodies is placed in the mixer, and mixed with 25 to 45 weight parts of "non-saturated" pure lactose (used for the purposes of cost reduction and simplification and acceleration of the technological process without decreasing the treatment efficiency), together with 0.1 to 1 weight parts of magnesium stearate, and 3 to 10 weight parts of microcrystalline cellulose. The obtained tablet mass is uniformly mixed, and tableted by direct dry pressing (e.g., in a Korsch-XL 400 tablet press) to form 150 to 500 mg round pills, preferably, 300 mg. After tableting, 300 mg pills are obtained that are saturated with aqueous-alcohol solution (3.0-6.0 mg/pill) of the activated-potentiated form of antibodies to CD4 receptor in the form of a mixture of centesimal homeopathic dilutions C12, C30, and C50 or a mixture of centesimal homeopathic dilutions C12, C30 and C200.

Preferably, for the purpose of treatment, the combination of the invention is administered from once daily to four times daily, preferably twice daily, each administration including one or two combination unit dosage forms.

The technological result sought by the claimed invention is the increased reliability and reproducibility of methods to identify medicaments prepared according to homeopathic techniques, i.e., medicaments that do not contain the molecular form in any practically detectable concentration. Further, the claimed invention seeks increased reliability and reproducibility of methods to determine the pharmacological modifying potency associated with a medicament, i.e., an activated-potentiated form. These methods are performed in vitro, i.e., outside the body.

Methods for achieving the technological result of this invention ultimately seek to determine the degree of modifying potency associated with the activated-potentiated form which was acquired during the activation process. Processing of the starting substance containing the molecular form to achieve a medicament prepared by homeopathic techniques, i.e., the activated-potentiated form, comprises multiple consecutive dilutions with a carrier, thus decreasing the concentration of the starting substance.

In the context of bipathic medicinal preparations, the potency of the activated-potentiated form is manifested in its ability to alter or affect the physical, chemical and/or biological properties of the therapeutic dose. That is, the claimed invention involves determining alterations in physical parameters of the therapeutic dose utilizing analytical methods after adding activated-potentiated form thereto. Such analytical methods will enable determination of the presence or absence the activated-potentiated form in the therapeutic dose. The analytical methods measure one or more physical parameters of the therapeutic dose prior to and after mixing with the activated-potentiated form. The degree of potency of the therapeutic dose prior to and after mixing with the activated-potentiated form can also be measured using analytical methods. Alterations of a characteristic parameter can be provided in relative units.

Measurement of a characteristic parameter could be affected by the presence of the molecular form at detectable levels in the activated-potentiated form. If molecules of the molecular form are present at detectable levels in the activated-potentiated form, then those molecules need to be removed from the activated-potentiated form prior to mixing the activated-potentiated form and the therapeutic dose. Absence of the molecular form in a sample is, for the purposes of the present subject matter, synonymous with inability to detect said molecular form. One means of removing/rendering undetectable molecular form from an activated-potentiated form is through further dilution, e.g., homeopathic centesimal dilution. Another means is through use of a molecular sieve. A molecular sieve is a material with very small holes of precise and uniform size. These holes are small enough to block large molecules while allowing small molecules to pass. Examples of molecular sieves include activated charcoal and silica gel. Similar to a molecular sieve, any procedure and/or apparatus having a tendency to stop or even slow down the molecular form while allowing the carrier to proceed can be utilized to remove or render undetectable the molecular form. Thus, a process like high-pressure liquid chromatography ("HPLC") can be used in which the immobile phase of the HPLC apparatus stops or slows the progress of the molecular form while the mobile phase, comprising the activated-potentiated form, proceeds through the apparatus relatively unimpeded. Depending on the parameters such as affinity of the molecular form for the solid phase, the molecular form will be completely absent from the output of the HPLC apparatus for at least some known period of time.

Additionally, if molecules of the starting substance are present in the modified solvent, they may be removed using well-established methods. In particular, the molecules of a protein taken as the starting substance may be removed, for example, by heating the modified solvent to achieve protein denaturation followed by filtration. Alternatively, a method of desalination may be used where the protein is precipitated by high concentrations of neutral salts of alkali and alkali earth metals followed by filtration. Other possible methods include electro dialysis, deionization using ion-exchange resins; reverse osmosis; and ultrafiltration (molecular filtration) with or without preliminary filtration through larger pores. By way of further examples found in the art, refer to B. M. Steward, *The production of high-purity water in the clinical laboratory*, Laboratory Medicine, vol. 31(11), pp. 605-611 (2000); J. Grimm, D. Bessarabov, R. Sanderson, *Review of electro-assisted method for water purification*, Desalination, vol. 115 (3), pp. 285-294 (1998); I. A. Koznacheev, et al., *Water purification of organic infusions in a reverse flow filtration combustion reactor*, International Journal of Heat and Mass Transfer, Vol. 54, pp. 932-937 (1998); Labconco Corporation, *A Guide to Laboratory Water Purification*, An Industry Service Publication. http://bioresearchonline.com/doc.mvc/A-Guide-to-Laboratory-WaterPurification.

The claimed method can be realized using different methods of quantitative and qualitative determination, thus ensuring high sensitivity and reproducibility in testing the presence and potency of an activated-potentiated form. Quantitative and qualitative methods include mass spectrometry such as chromatography mass-spectrometry, gas liquid chromatography ("GLC") and high-performance liquid chromatography ("HPLC"); NMR spectroscopy, immune enzyme assay ("IEA").

Chromatography is based on partition of components of a mixture caused by the difference of their homogenous distribution between two immiscible phases. One phase in chromatography is immobile (sorbent) while another one is mobile (eluent). High pressure (up to 400 bar) and solvent slurry (generally 3-5 µm; at present it is up to 1.8 µm) are distinguishing features of HPLC. Qualitative determination using HPLC analysis is based on evaluation of retention time of chromatography peak. Quantitative determination is based on peak area evaluation.

Nuclear magnetic resonance spectroscopy ("NMR spectroscopy") is a research technique that exploits the magnetic properties of certain atomic nuclei. NMR determines the physical and chemical properties of atoms or the molecules in which they are contained. It relies on the phenomenon of nuclear magnetic resonance and can provide detailed information about the structure, dynamics, reaction state, and chemical environment of molecules. The intramolecular magnetic field around an atom in a molecule changes the resonance frequency, thus giving access to details of the electronic structure of a molecule. Software allows analysis of signal intensity of peaks, which under conditions of optimal relaxation, correlate with the number of protons of that type. Analysis of signal intensity is done by integration—the mathematical process that calculates the area under a curve, its size is dependent on its area.

An immune enzyme assay ("IEA") is a biochemical test that measures the presence or concentration of a macromolecule in a solution through the use of an antibody or immunoglobulin. The macromolecule detected by the immunoassay is often referred to as an "analyte". Ideally, the antibody will bind to the analyte and only the analyte. Once bound to the analyte, the antibody emits a signal indicative of the presence of a single molecule of analyte. Such a signal might be the immediate spontaneous release of a photon of light upon binding or the release of a photon of light by analyte bound antibodies upon occurrence of some 'polling' signal. Similarly, analyte bound antibodies might react differently than unbound antibodies to a later step of IEA allowing, e.g., for removal of the unbound antibodies and assessment of the number of bound antibodies remaining.

Further, antibodies may be bound to a piezoelectric crystal which undergoes elastic deformation when an electrical current is applied to it. An alternating electrical current (A.C.) produces a standing wave in the crystal of a characteristic frequency. The frequency is highly dependent on the elastic properties of the crystal, which properties are affected by what is attached to the crystal. The binding of a target analyte to an antibody will produce a change in the resonance frequency, which gives a binding signal. Biological and other methods are applicable for realization of the claimed method. See, e.g., Zolotov, Yu. A. (editor), *Basics of analytical chemistry* (in 2 volumes), Textbook for universities, 3$^{rd}$ edition (2004); Vasilyev, V. P., *Analytical chemistry*, (1989); Otto, M., *Up-to-date methods of analytical chemistry*, (2003).

Using a combination of analytical methods to detect the molecules of the starting substance in the said activated-potentiated carrier and measurement by analytical methods of at least one characteristic parameter of the starting substance before and after its interaction with the said activated-potentiated carrier, we demonstrate (substantiate) that: first, the modifying activity associated with the carrier is not accounted for by the presence of molecules of the starting substance, and that the physical, chemical and/or biological properties of the said carrier differ from the physical, chemical and/or biological properties of the starting substance; secondly, the activated-potentiated carrier is obtained by using the starting substance, where the activated-potentiated form is ensured by the very procedure employed during the technological treatment of the starting substance and represented by multiple serial concentration reduction of the latter with the use of the said carrier. Finally, based on in vitro evidence, the authenticity and identity is demonstrated for the drug product prepared using the said activated-potentiated carrier. That is, beginning with the molecular form in therapeutic concentration the activated-potentiated form is made through multiple consecutive decreasing of the concentration of the molecular form using the carrier. Further, the claimed analytical measurement of at least one characteristic parameter of the therapeutic form prior to its interaction with the activated-potentiated form and again after such interaction serves to quantify the degree of modifying potency associated with the activated-potentiated form in relative dimensionless activity units (release activity).

The degree of modifying potency pertaining to an activated-potentiated form is determined based on quantitative alterations of a characteristic parameter expressed in relative activity units (release activity), formula (1):

$$X = C|A - A_M|/A \quad (1)$$

X is the number of activity units (AU);

C is a dimensionless constant of proportionality which is contingent on analytical methods used for measuring the characteristic parameter that reflects the initial physical, chemical and/or biological properties of the starting substance and on the characteristic parameter value. In particular, for example, $C = 10^k$, where k is an integer from the sequence 1, 2, 3 etc.;

A is the value of a characteristic parameter of the starting substance prior to its interaction with the said activated-potentiated form (technologically treated carrier);

$A_M$ is the value of the same characteristic parameter of the starting substance after its interaction with the said activated-potentiated form (technologically treated carrier).

The claimed method can be realized using different methods of quantitative and qualitative determination, thus ensuring high sensitivity and reproducibility in testing ultralow substance concentrations, such as spectrometry, particularly mass spectrometry, chromatography mass-spectrometry (gas liquid chromatography (GLC)) and high-performance liquid chromatography (HPLC) based on separation of components of a mixture caused by the difference of their homogenous distribution between two immiscible phases. One phase in chromatography is immobilized (sorbent) and the other one is mobile (eluent). High pressure (up to 400 bars) and sorbent slurry (generally 3-5 µm; here up to 1.8 µm) are distinguishing features of HPLC. Qualitative determination using HPLC analysis is based on evaluation of retention time of chromatography peak. Quantitative determination is based on peak area evaluation.

Another technique used in the realization of the claimed method is nuclear magnetic resonance spectroscopy (NMR spectroscopy) that exploits the magnetic properties of certain atomic nuclei. NMR determines the physical and chemical properties of atoms or the molecules in which they are contained. It relies on the phenomenon of resonance absorption and emission of electromagnetic energy by substances with zero-spin nuclei when placed in an external magnetic field at a frequency ν (so-called NMR frequency) which is induced by reorientation of magnetic nuclear moments, where a so-called chemical shift is the characteristic parameter. Further, the mentioned techniques include an immune enzyme assay (IEA), the use of a piezoelectric immunosensor the analytical signal of which is represented by a difference in the resonance frequency of the piezoelectric resonator (Δf) resulting from weight increases or decreases of the receptor-covered layer due to formation and destruction of immune complex on its surface. Biological and other methods are also applicable for the realization of the claimed method (e.g., see Zolotov, Yu. A. (editor), *Basics of analytical chemistry* (2 volumes), Textbook for universities, 3$^{rd}$ edition, revised and supplemented: Vysshaya shkola Publisher (2004); Vasilyev, V. P., *Analytical chemistry*, (1989); Otto, M., *Up-to-date methods of analytical chemistry*, (2003).

Additionally, if molecules of the starting substance are present in the modified solvent, they may be removed using well-established methods. In particular, the molecules of a protein taken as the starting substance may be removed, for example, by heating the modified solvent to achieve protein denaturation followed by filtration. Alternatively, a method of desalination may be used where the protein is precipitated by high concentrations of neutral salts of alkali and alkali earth metals followed by filtration. Other possible methods include electro dialysis, deionization using ion-exchange resins; reverse osmosis; and ultrafiltration (molecular filtration) with or without preliminary filtration through larger pores. By way of further examples found in the art, refer to B. M. Steward, The production of high-purity water in the clinical laboratory//Laboratory Medicine.-2000.-V. 31(11)-P. 605-611; J. Grimm, D. Bessarabov, R. Sanderson. Review of electro-assisted methods for water purification//Desalination.-1998.-V. 115 (3)-P. 285-294; I. A. Koznacheev, et al., Water purification of organic inclusions in a reverse flow filtration combustion reactor//International Journal of Heat and Mass Transfer-1998. 54-P. 932-937; Labconco Corporation, A guide to laboratory water purification, An Industry Service Publication. http://bioresearchonline.com/.

Using a combination of analytical methods to detect the molecules of the starting substance in the said activated-potentiated carrier and measurement by analytical methods of at least one characteristic parameter of the starting substance before and after its interaction with the said activated-potentiated carrier, we demonstrate (substantiate) that: first, the modifying activity associated with the carrier is not accounted for by the presence of molecules of the starting substance, and that the physicochemical and/or biological properties of the said carrier differ from the physicochemical and/or biological properties of the starting substance; secondly, the activated-potentiated carrier is obtained by using the starting substance, where the activated-potentiated form is achieved through the very procedure employed during the technological treatment of the starting substance, i.e. multiple serial concentration reduction of the latter with the use of the said carrier. Finally, based on in vitro evidence, the authenticity and identity is demonstrated for the drug product prepared using the said activated-potentiated carrier.

Further, the claimed analytical measurement of at least one characteristic parameter of the starting substance before and after its interaction with the activated-potentiated carrier serves to quantify the degree of modifying potency associated with the carrier in relative dimensionless activity units (release activity).

To determine the degree of modifying potency associated with the carrier, the following consecutive procedures are performed:

a. preparation of the carrier with modifying activity potentized in the course of technological processing (treatment) of the starting substance by multiple steps of serial concentration reduction using the said carrier, where the latter does not contain molecular form of the said starting substance.

b. specificity testing of the substance present in the solution from step a, which includes i. treatment of the molecular form of the starting substance with the carrier stated in step a.)

ii. preferably, treatment of the molecular form of a different substance and/or solvent with the carrier stated in step a.)

iii. analytical measurement of at least one physicochemical and/or biological characteristic parameter of the said molecular form of the starting substance (A) and the said combination under paragraph b.) i.) ($A_M$), where the said carrier specifically modifies the effect-capacity to modify the physicochemical and/or biological properties of the starting substance is considered specific to the substance if the change in the said characteristic parameter with the realization of paragraph b.)i.) is statistically significant (and is not statistically significant with realization of paragraph b.)ii.))

c. determination of the modifying potency associated with the carrier in relative activity units using equation (1):

$$X = C|A - A_M|/A \tag{1}$$

X, C, A and $A_M$ are as defined previously where C is preferably equal to 100 or 1000.

EXAMPLES

The present invention is now illustrated by the following Examples, which do not limit the scope of the invention in any way.

Abbreviations generally used in the Examples:
Ab—antibodies
ELISA or IEA—solid-phase enzyme immunoassay
OD—optical density
IFN-gamma—interferon gamma
HPLC—high-performance liquid chromatography
AC—activated-potentiated form
PBS—phosphate-buffered saline
APBS—phosphate-buffered saline activated according to homeopathic technique
IgG—immunoglobulin G, including antibodies to interferon gamma ("IFN-gamma")
A water—water activated according to homeopathic technique
UV/Vis—Ultraviolet to visible spectroscopy

Example 1

The purpose of Example 1 is to determine the degree of modifying potency of the activated-potentiated form of rabbit Ab to human IFN-gamma. Beginning with a mother solution of rabbit Ab to human IFN-gamma, an activated-potentiated form of rabbit Ab to human IFN-gamma was prepared by multiple consecutive dilutions decreasing of concentration of the starting substance accompanied by multiple intermediate shaking. The diluent, i.e., carrier, was a water-alcohol solution. The molecular form was diluted in $100^{12}$, $100^{30}$ and $100^{50}$ parts carrier, i.e., centesimal homeopathic dilutions C12, C30, C50. To determine alterations of physical, chemical and/or biological properties of the starting substance, i.e., rabbit Ab to human IFN-gamma, HPLC was applied while substance volume was used as characteristic parameter.

Substance quantitative determination was based on evaluation of peak area value using HPLC. Mixture of IgG+AC was chosen as test sample. As control samples the following mixtures were used: IgG+A water, IgG+water and IgG+APBS.

Test samples were prepared by mixing IgG (50 mg/ml) and AC (or A water or APBS or water) in the ratio 1:2 (v/v). Resultant mixtures were filtered using cellulose acetate membrane filters, pore size—0.45 µm.

Analysis was performed with HPLC separation in gradient mode. Anion-exchange column was applied as stationary phase; mixture of 2 phases (phase 1—acetonitrile, phase 2—potassium hydrogen phosphate solution and potassium chloride solution) were used as mobile phase. UV-Vis detector was applied for detection purpose; wavelength—280 nm.

Calibration and zero setting of baseline of UV-Vis detector were conducted prior to each analysis and after it.

Prepared mixtures were transferred into vials and were introduced into chromatography system using auto-sampler. Analysis time for each test sample was about 23 minutes.

Upon completion of the analysis chromatographic column equilibration was run at a constant flow rate under the conditions of mobile phase gradient similar to the ones at the beginning of the analysis.

Signal emitted by test samples was registered in the form of peaks chromatogram, which are supposed to correspond to light and heavy IgG chains. Area of spectrophotometric peak first maximum (Max-1 corresponds to immunoglobulin heavy chains) and second maximum (Max-2 corresponds to immunoglobulin light chains) was calculated. The results of this analysis are presented in Table 1.

TABLE 1

Areas of chromatographic peak maximum

| Test sample | Area of chromatographic peak maximum | | Substance modifying potency in AU at C = 100 | |
|---|---|---|---|---|
| | Max-1 | Max-2 | Max-1 | Max-2 |
| IgG + AC | 17207.9 ± 434.7 | 45860.6 ± 9427.3 | | |
| IgG + water | 30270.2 ± 980.6 | 5577.4 ± 467.5 | 43.2 | 722.3 |
| IgG + A water | 28704.0 ± 4265.3 | 5626 ± 686.6 | 40.1 | 715.2 |
| IgG + APBS | 25888.7 ± 1514.1 | 7135.7 ± 746.0 | 33.5 | 542.7 |

The degree of modifying potency is calculated applying equation (1):

$$(X = C|A - A_M|/A)$$

where C=100. Equation (1) is applied to the IgG+AC sample and the IgG+water sample, resulting in:

$$A = 30270.2; A_M = 17207.9; X = 43.2 AU; \quad \text{(Max-1)}$$

$$A = 5577.4; A_M = 45860.6; X = 722.3 AU \quad \text{(Max-2)}$$

Experiments show that AC to IFN-gamma decreases area of IgG peak first maximum (Max-1 corresponds to immunoglobulin heavy chains) and increases area of IgG peak second maximum (Max-2 corresponds to immunoglobulin light chains) as compared to controls.

The results of Example 1 support the following conclusions:

1. Due to technique used for preparation of C12, C30, C50 homeopathic dilutions, an activated-potentiated form comprising a mixture of these three homeopathic dilutions a priori does not contain molecules of the starting substance;

2. Alterations of physical and chemical properties of the starting substance rabbit Ab to human IFN-gamma, treated by the activated-potentiated form present reliable evidence that the said activated-potentiated form is prepared on the basis of the starting substance—IFN-gamma;

3. Alterations of physical and chemical properties of the starting substance, rabbit Ab to human IFN-gamma, treated by the activated-potentiated form significantly validate the degree of modifying potency associated with activated-potentiated form and provides opportunity for expressing the said modifying potency revealed by using HPLC technique in dimensionless activity units according to equation (1) (Table 1).

Example 2

The purpose of Example 2 is to determine the degree of modifying potency of the activated-potentiated form of rabbit Ab to human IFN-gamma. Beginning with a mother solution of rabbit Ab to human IFN-gamma, an activated-potentiated form of rabbit Ab to human IFN-gamma was prepared by multiple consecutive dilutions decreasing of concentration of the starting substance accompanied by multiple intermediate shaking. The diluent, i.e., carrier, was a water-alcohol solution. The molecular form was diluted in $100^{12}$, $100^{30}$ and $100^{50}$ parts carrier, i.e., centesimal homeopathic dilutions C12, C30, C50. To determine alterations of physical, chemical and/or biological properties of the starting substance, i.e., rabbit Ab to human IFN-gamma, HPLC was applied while substance volume was used as characteristic parameter.

Substance quantitative determination was based on evaluation of peak area value using HPLC. Mixture of Ab to IFN-gamma+AC was chosen as test sample. As control samples the following mixtures were used: Ab to IFN-gamma+A water, Ab to IFN-gamma+water and Ab to IFN-gamma+APBS.

Test samples were prepared by mixing Ab to IFN-gamma and AC (or A water or APBS or water) in the ratio 1:1 (v/v). The resultant mixtures were vortexed for 15 seconds, incubated at room temperature for 18 hours and then AC, A water, APBS or water was added.

Analysis was performed with HPLC separation in gradient mode. Reverse-phase octadecysilane column was applied as stationary phase; mixture of 2 phases (phase 1—acetonitrile supplemented with acetic-acid and trifluoroacetic acid, phase 2—deionized water with methyl acid and trifluoroacetic acid) were used as mobile phase. UV-Vis detector was applied for detection purpose; wavelength—280 nm.

Calibration and zero setting of baseline of UV-Vis detector were conducted prior to each analysis and after it.

Prepared mixtures were transferred into vials and were introduced into chromatography system using auto-sampler. Analysis time for each test sample was about 15 minutes.

Upon completion of the analysis chromatographic column equilibration was run at a constant flow rate under the conditions of mobile phase gradient similar to the ones at the beginning of the analysis.

Signal emitted by test samples was registered in the form of peaks chromatogram of the corresponding protein. Area of spectrophotometric peak was calculated. The results of this analysis are presented in Table 2.

TABLE 2

Area of chromatographic peak maximum

| Test sample | Area of chromatographic peak | Substance modifying potency in AU at C = 100 |
|---|---|---|
| Ab to INF-gamma + AC form of Ab to IFN-gamma | 113.1 ± 3.6 | |
| Ab to INF-gamma + A water | 123.2 ± 3.6 | 8.2 |
| Ab to INF-gamma + water | 128.3 ± 0.3 | 11.8 |

It was shown that the activated-potentiated form of Ab to IFN-gamma reduce peak area of Ab to IFN-gamma as compared to controls.

The results of Example 1 support the following conclusions:

1. Due to technique used for preparation of C12, C30, C50 homeopathic dilutions, an activated-potentiated form comprising a mixture of these three homeopathic dilutions a priori does not contain molecules of the starting substance;

2. Alterations of physical and chemical properties of the starting substance, rabbit Ab to human IFN-gamma, treated by the activated-potentiated form significantly validate that the said activated-potentiated form is prepared on the basis of the starting substance—Ab to interferon gamma (anti-IFN-gamma);

3. Alterations of physical and chemical properties of the starting substance, rabbit Ab to human IFN-gamma, treated by the activated-potentiated form significantly validate the degree of modifying potency associated with activated-potentiated form and provides opportunity for expressing the said modifying potency revealed by using HPLC technique in dimensionless activity units according to equation (1) (Table 2).

Example 3

The purpose of Example 3 is to determine the degree of modifying potency of the activated-potentiated form of diclofenac sodium. Beginning with a mother solution of diclofenac sodium, an activated-potentiated form of diclofenac sodium was prepared by multiple consecutive dilutions decreasing of concentration of the starting substance accompanied by multiple intermediate shaking. The diluent, i.e., carrier, was a water-alcohol solution. The molecular form was diluted in $100^{12}$, $100^{30}$ and $100^{200}$ parts carrier, i.e., centesimal homeopathic dilutions C12, C30, C200. To determine alterations of physical, chemical and/or biological properties of the starting substance, i.e., diclofenac sodium, HPLC was applied while substance volume was used as characteristic parameter.

Substance quantitative determination was based on evaluation of peak area value using HPLC. Mixture of diclofenac+lactose, saturated with AC was chosen as test sample. As control samples the following mixtures were used: diclofenac+lactose, saturated with APBS, and diclofenec+non-saturated lactose.

Test samples were presented in the form of diclofenac sodium powder, non-saturated lactose and lactose saturated with AC (APBS). Powders were dissolved in distilled water, the ratio of diclofenac weighted amount and lactose weighted amount was 1:3; volume of water used for dissolution was identical. Prepared solutions were mixed with diclofenac sodium solution in the ratio 1:3 (v/v). The solutions were mixed by vertical manual shaking of vials for 15 seconds. Bidistillate was used to dilute mixture of solutions to achieve final concentration 0.3 μg/ml. The solutions were subjected to manual stirring for 15 seconds by vertical shaking of flasks. Resultant mixtures were incubated in dark place at room temperature for 18 hours.

Analysis was performed with HPLC separation in gradient mode. Column packed with silica gel and modified with octadecyl was applied as stationary phase; mixture of 2 phases (phase 1—distilled water with formic acid and trifluoroacetic acid, phase 2—acetonitrile with formic acid and trifluoroacetic acid) were used as mobile phase. UV-Vis detector was applied for detection purpose; wavelength—276 nm.

Calibration and zero setting of baseline of UV-Vis detector were conducted prior to each analysis.

Prepared mixtures were transferred into vials and were introduced into chromatography system using auto-sampler. Analysis time for each test sample was about 15 minutes.

Upon completion of the analysis chromatographic column equilibration was run at a constant flow rate under the conditions of mobile phase gradient similar to the ones at the beginning of the analysis.

Signal emitted by test samples was registered in the form of peaks chromatogram corresponding to diclofenac. Area of spectrophotometric peak was calculated. The results of this analysis are presented in Table 3 (detection was conducted at 276 nm).

TABLE 3

Area of chromatographic peak maximum

| Test sample | Area of chromatographic peak | Substance modifying potency in AU at C = 100 |
|---|---|---|
| Diclofenac + lactose saturated with AC | 66039.3 ± 549.1 | |
| Diclofenac + lactose saturated with APBS | 42652.0 ± 484 .2 | 54.8 |
| Diclofenac + non-saturated lactose | 32004.3 ± 1113.7 | 106.3 |

It was shown that peak area of diclofenac mixed with AC exceeds peak area of diclofenac mixed with controls, i.e., non-saturated lactose and lactose saturated with APBS.

The results of Example 3 support the following conclusions:

1. Due to technique used for preparation of C12, C30, C50 homeopathic dilutions, an activated-potentiated form comprising a mixture of these three homeopathic dilutions a priori does not contain molecules of the starting substance;

2. Alterations of physical and chemical properties of the starting substance, diclofenac, treated by the activated-potentiated form of diclofenac, significantly validate that the said activated-potentiated form is prepared on the basis of the starting substance—diclofenac;

3. Alterations of physical and chemical properties of the starting substance, diclofenac, treated by the activated-potentiated form of diclofenac significantly validate the degree of modifying potency associated with activated-potentiated form and provides opportunity for expressing the said modifying potency revealed by using HPLC technique in dimensionless activity units according to equation (1) (Table 3).

Example 4

The purpose of Example 4 is to determine the degree of modifying potency of the activated-potentiated form of rabbit Ab to human IFN-gamma. Beginning with a mother solution of rabbit Ab to human IFN-gamma, an activated-potentiated form of rabbit Ab to human IFN-gamma was prepared by multiple consecutive dilutions decreasing of concentration of the starting substance accompanied by multiple intermediate shaking. The diluent, i.e., carrier, was a water-alcohol solution. The molecular form was diluted in $100^{12}$, $100^{30}$ and $100^{50}$ parts carrier, i.e., centesimal homeopathic dilutions C12, C30, C50. To determine alterations of physical, chemical and/or biological properties of the starting substance, i.e., rabbit Ab to human IFN-gamma, ELISA was applied while alteration in the number of antigen-antibody complexes was used as characteristic parameter.

Prior to carrying out the analysis, Ab to IFN-gamma and AC (or APBS used as placebo) were preincubated for 24 hours at 4° C.; during incubation Ab to IFN-gamma bound with IFN-gamma contained in the solution. After incubation, each sample was exposed to an ELISA plate having a solid phase antigen surface. Ab to IFN-gamma previously bound to IFN-gamma were adsorbed onto the solid phase of the ELISA plate. The Ab to IFN-gamma remaining unbound to IFN-gamma after incubation remained in solution.

Resultant samples were tested in accordance with ELISA procedures. The number of formed antigen-antibody complexes adsorbed onto the solid phase was determined by measuring solutions optical density in plate wells taking into consideration reaction of extinction of chromogen solution, which color changes on the background of enzyme—induced decomposition of substrate. To determine solution extinction spectrophotometric technique at wavelength 490 nm in a single—wave mode was applied. The more antigen-antibody complexes were formed on a plate the less Ab to IFN-gamma bound with IFN-gamma in the solution.

Mean OD of samples for 2 similar experiments incubated with AC was 0.603±0.075 (when AC or placebo were immediately mixed with antigen and with Ab to IFN-gamma and were incubated for 24 hours) or 0.251±0.027 (when AC or placebo were mixed with Ab to IFN-gamma while upon 40 minute incubation antigen was added and 24 hour incubation was conducted) while for IFN-gamma incubated with APBS optical density values were 0.812±0.084 and 0.391±0.023 respectively.

The experiments have shown that AC water solutions decrease number of antigen-antibody complexes in the solution as compared to control, which validate identity of the drug containing rabbit antibodies to human interferon—gamma (Ab to IFNγ).

The results of Example 4 support the following conclusions:

1. Due to technique used for preparation of C12, C30, C50 homeopathic dilutions, an activated-potentiated form comprising a mixture of these three homeopathic dilutions a priori does not contain molecules of the starting substance;

2. Alterations of physical and chemical properties of the starting substance, rabbit Ab to human IFN-gamma, treated by the activated-potentiated form significantly validate that the said activated-potentiated form is prepared on the basis of the starting substance—Ab to interferon gamma (anti-IFN-gamma);

3. Alterations of physical and chemical properties of the starting substance, rabbit Ab to human IFN-gamma, treated by the activated-potentiated form significantly validate the degree of modifying potency associated with activated-potentiated form and provides opportunity for expressing the said modifying potency revealed by using HPLC technique in dimensionless activity units according to equation (1) (Table 2). The degree of modifying activity calculated using equitation (1) (as compared to placebo) was 25.7-35.8 AU.

Example 5

The purpose of Example 5 is to determine the degree of modifying potency of the activated-potentiated form of rabbit Ab to human IFN-gamma. Beginning with a mother solution of rabbit Ab to human IFN-gamma, an activated-potentiated form of rabbit Ab to human IFN-gamma was prepared by multiple consecutive dilutions decreasing of concentration of the starting substance accompanied by multiple intermediate shaking. The diluent, i.e., carrier, was a water-alcohol solution. The molecular form was diluted in $100^{12}$, $100^{30}$ and $100^{50}$ parts carrier, i.e., centesimal homeopathic dilutions C12, C30, C50. To determine alterations of physical, chemical and/or biological properties of the starting substance, i.e., rabbit Ab to human IFN-gamma, the ability of antibodies adsorbed on a piezoelectric immunosensor surface to bind with antigen treated by the activated-potentiated form was measured.

Abbreviations specific to Example 5:

Δf—alterations of oscillation frequency of piezoelectric immunosensor

APTS—γ-aminopropyltriethoxysilane $S_r$—standard deviation

An analytical signal of a piezoelectric immunosensor comprises a change in oscillation frequency (Δf) of a quartz crystal resonator depending on increase or decrease in bioreceptor mass. Such a mass change may arise from the formation or destruction of an immune complex on the sensor surface. During the given study the effect of composition of analyzed samples on sensor analytical signal was evaluated. A mixture of IFN-gamma and activated-potentiated form ("AC") of IFN-gamma was chosen as test sample. A mixture of IFN-gamma and APBS was used as a control sample. Samples were tested in the form of aqueous solutions.

To create the immunosensor, an APTS-based bio-recognition receptor layer was formed on a piezoelectric element. Using micro syringe surface of sensor gold electrode (diameter 8 mm) was consequently coated with 0.8 µl APTS (it was dried in an exsiccator for 20 minute at 80° C.), 5 µL glutaraldehyde (2.5% solute in distilled water) and then 5 µl solution of antibodies to IFN-gamma (9.6 ng/ml). For each measurement a new bio-recognition receptor layer was formed.

Preliminary sample preparation included mixing of 50 µl of IFN-gamma (30 mg/ml) with 50 µl test sample. The sample was then heated for 45 minutes at 37° C. and was mixed for 10 minutes by centrifugation (1000 rpm). The sensor surface with immobilized Ab to IFN-gamma was coated with 2.5 µl of resultant solution, kept for 30 minutes, washed by distilled water, dried to acquire constant weight and measurement of sensor static signal was conducted. Alterations of antigen-antibody binding were evaluated from mass alteration of interferon molecule.

Piezoelectric resonators made from an AT-cut quartz crystal with 8 mm gold electrode (ZAO ETNA, Moscow) were used as sensors. To register analytical signal personal computer and DiScope transducer (NPP Bafika, Moscow) were applied.

The experiment results are presented in Table 4.

TABLE 4

The effect of test sample composition on sensor analytical signal

| Sample composition | Δf (M ± SD) | Substance modifying potency in AU at C = 100 |
|---|---|---|
| IFN-gamma + AC | 89 ± 4 | |
| IFN-gamma + APBS | 123 ± 5 | 2764.2 |

The experiments have shown that adding the activated-potentiated form to therapeutic form of IFN-gamma affects the frequency of piezoelectric resonator inducing its reduction as compared to controls.

The results of Example 5 support the following conclusions:

1. Due to technique used for preparation of C12, C30, C50 homeopathic dilutions, an activated-potentiated form comprising a mixture of these three homeopathic dilutions a priori does not contain molecules of the starting substance;

2. Alterations of physical and chemical properties of the starting substance, IFN-gamma, treated by the activated-potentiated form significantly validate that the said activated-potentiated form is prepared on the basis of the starting substance—Ab to interferon gamma (anti-IFN-gamma);

3. Alterations of physical and chemical properties of the starting substance, rabbit Ab to human IFN-gamma, treated by the activated-potentiated form significantly validate the degree of modifying potency associated with activated-potentiated form and provides opportunity for expressing the said modifying potency revealed by using a piezoelectric sensor in dimensionless activity units according to equation (1) (Table 4). The degree of modifying activity calculated using equitation (1) (as compared to placebo) was 2764.2 AU.

Example 6

Analysis of alterations of neutralizing activity of antibodies to IFN-gamma treated by release active antibodies to IFN-gamma; applied method is measurement of neutralizing activity.

The purpose of Example 6 is to determine the degree of modifying potency of the activated-potentiated form of rabbit Ab to human IFN-gamma. Beginning with a mother solution of rabbit Ab to human IFN-gamma, an activated-potentiated form of rabbit Ab to human IFN-gamma was prepared by multiple consecutive dilutions decreasing of concentration of the starting substance accompanied by multiple intermediate shaking. The diluent, i.e., carrier, was a water-alcohol solution. The molecular form was diluted in $100^{12}$, $100^{30}$ and $100^{50}$ parts carrier, i.e., centesimal homeopathic dilutions C12, C30, C50. To determine alterations of physical, chemical and/or biological properties of the starting substance, i.e., rabbit Ab to human IFN-gamma, the alteration of neutralizing activity of Ab to IFN-gamma treated by activated-potentiated form of Ab to IFN-gamma was used while alteration in the number of survived cells after viral infection was used as characteristic parameter.

Abbreviations specific to Example 6:
R (X)—RPM1-1640, culture medium containing X %—fetal calf serum
NA—neutralizing activity
CPE—cytopathic effect Neutralizing activity, measured as NA/ml, of the drugs containing antibodies is based on inhibition of IFN-gamma binding with its receptor expressed on the cell membrane.

Neutralizing activity of samples of polyclonal rabbit Ab to IFN-gamma in cultural medium [R(1)] in the presence of activated-potentiated form ("AC") or a control sample (distilled water).

Cultured human embryonic lung fibroblast HEp-2 cells were trypsinized, suspended in 10 ml R(10) and were plotted on a plate at concentration $2.3 \times 10^5$ cells/well (100 µl/well). The cells were incubated 24 hours at 37° C. in a humidified incubator with 7% $CO_2$. IFN-gamma was subjected to step by step dilution in R(1), from 500 ng/ml to 3.9 ng/ml and inserted into wells. Rabbit polyclonal antibodies to IFN-gamma (2 consecutive dilution in (1) starting from millesimal dilution) and mixed with IFN-gamma in fixed concentration (250 ng/ml) and AC (10% (v/v) in R(1)) or in distilled water (10% (v/v in R(1)). Plates were incubated 1 hour at 37° C.

After incubation, the wells were emptied and vesicular stomatitis virus in R(1) in the amount of 100 µl/well was added. After that cells were incubated for 20-24 hours at 37° C. until CPE in control line wells exceeded 90%.

Upon removal of cultured medium the remaining cells were washed with PBS (200 µl/well) and treated with crystal violet in formalin (50 µl/well) for 15 minutes at room temperature. Monolayer 100% staining was observed when all cells were alive; if cells were dead (CPE) no monolayer staining was observed.

The plate was washed with water. Wells with dilutions demonstrating about 50% CPE were visually identified and then were tested using spectrophotometry.

The effect evaluation is based on the number of surviving cells (ratio of surviving cell to the total number of cells). Reduction of neutralizing activity of Ab to IFN-gamma was considered to be criteria of evaluation of activated-potentiated form effect. To calculate drugs neutralizing activity the following equation was applied: F×A×10/C, where F=the reciprocal value of antibodies dilution, A=EU/ml of standard drug at 50% CPE, and C=antibodies concentration (mg/ml).

The experiment has shown that:
- when incubating human IFN-gamma (500 ng/1 ml of culture medium) with human embryonic fibroblast, lung-derived cell line HEp-2 cells ($2.3 \times 10^5$ cells/well) infected with vesicular stomatitis virus ($1.6 \times 10^5$ PFU/ml), complete inhibition of virus cytopathic effect was seen (100% of infected cells survived);
- when incubating human IFN-gamma (500 ng/1 ml of culture medium) and rabbit polyclonal Ab to IFN-gamma (0.525 µg/1 ml of culture medium) with human embryonic fibroblast, lung-derived cell line HEp-2 cells ($2.3 \times 10^5$ cells/well) infected with vesicular stomatitis virus ($1.6 \times 10^5$ PFU/ml), 50% inhibition of virus cytopathic effect was seen (50% of infected cells survived);
- when incubating human IFN-gamma (500 ng/1 ml of culture medium) and rabbit polyclonal Ab to IFN-gamma (0.525 µg/1 ml of culture medium), as well as the activated-potentiated form (10% (v/v) of culture medium) human embryonic fibroblast, lung-derived cell line HEp-2 cells ($2.3 \times 10^5$ cells/well) infected with vesicular stomatitis virus ($1.6 \times 10^5$ PFU/ml), 75% inhibition of virus cytopathic effect was seen (75% of infected cells survived);

At that it was revealed that the activated-potentiated form caused modulating effect on polyclonal antibodies modulating activity.

The results of Example 6 support the following conclusions:

1. Due to technique used for preparation of C12, C30, C50 homeopathic dilutions, an activated-potentiated form comprising a mixture of these three homeopathic dilutions a priori does not contain molecules of the starting substance;

2. Alterations of physical and chemical properties of the starting substance, rabbit Ab to human IFN-gamma, treated by the activated-potentiated form significantly validate that the said activated-potentiated form is prepared on the basis of the starting substance rabbit Ab to human IFN-gamma;

3 Alterations of physical and chemical properties of the starting substance treated by the above—said activated-potentiated form significantly validate the degree of modifying potency associated with carrier and provides opportunity for expressing the said modifying potency in dimensionless activity units according to equation (1), which, based on neutralizing activity measurements, was equal to 50 AU.

Example 7

The purpose of Example 7 is to determine the degree of modifying potency of the activated-potentiated form of rabbit Ab to human IFN-gamma. Beginning with a mother solution of rabbit Ab to human IFN-gamma, an activated-potentiated form of rabbit Ab to human IFN-gamma was prepared by multiple consecutive dilutions decreasing of concentration of the starting substance accompanied by multiple intermediate shaking. The diluent, i.e., carrier, was a water-alcohol solution. The molecular form was diluted in $100^{12}$, $100^{30}$ and $100^{50}$ parts carrier, i.e., centesimal homeopathic dilutions C12, C30, C50. To determine alterations of physical, chemical and/or biological properties of the starting substance, i.e., rabbit Ab to human IFN-gamma, by activated-potentiated form of Ab to human IFN-gamma, spectroscopy and NMR were used while information on substance molecular structure was used as characteristic parameter.

To determine conformational alterations of antibodies to IFN-gamma (Ab to IFN-gamma) treated by the activated-potentiated form ("AC"), NMR spectroscopy was applied. Homeopathic dilutions of purified water were used as control.

To prepare test samples AC or purified water was mixed with solution of Ab to IFN-gamma in the ratio 2:1. The final concentration of Ab to IFN-gamma in each sample was 0.8 mg/ml.

A Brucker Avance 700 (operating frequency 700 MHg) NMR instrument was used to conduct the experiment. Test samples were introduced into the device magnetic field. The excitation of magnetic hydrogen isotope 1H was observed. Signal of test samples was registered in the form of NMR spectra (signal accumulation for 12 hours), which characterizes structure and conformational state of Ab to IFN-gamma.

Evaluation of conformational condition of Ab to IFN-gamma was conducted in the framework of comparative analysis of spectra acquired from the sample containing Ab to IFN-gamma+AC or Ab to IFN-gamma+purified water. Comparison was conducted by spectral overlap upon the appropriate scaling.

The study results showed that adding the activated-potentiated form to Ab to IFN-gamma caused alterations of spectrum of Ab to IFN-gamma in the 8-8.5 ppm, 7.6-7.8 ppm, 6-6.6 ppm range as compared to spectrum of Ab to IFN-gamma+purified water. FIG. 1 shows overlap of spectra of Ab to IFN-gamma+AC and Ab to IFN-gamma+purified water.

The experiment has shown that the activated-potentiated form affects Ab to IFN-gamma conformation in solution.

The results of Example 7 support the following conclusions:

1. Due to technique used for preparation of C12, C30, C50 homeopathic dilutions, an activated-potentiated form comprising a mixture of these three homeopathic dilutions a priori does not contain molecules of the starting substance;

2. Alterations of physical and chemical properties of the starting substance, rabbit Ab to human IFN-gamma, treated by the activated-potentiated form significantly validate that the said activated-potentiated form is prepared on the basis of the starting substance rabbit Ab to human IFN-gamma;

3. Alterations of physical and chemical properties of the starting substance treated the said activated-potentiated form significantly validate the degree of modifying potency associated with activated-potentiated form.

The description, examples and drawings contained herein represent the presently preferred embodiment of the invention and are, as such, a representative of the subject matter which is broadly contemplated by the present invention. The scope of the present invention fully encompasses other embodiments that may become obvious to those skilled in the art, and the scope of the present invention is accordingly limited by nothing other than the appended claims.

What is claimed is:

1. A method for quantitatively determining activity of activated-potentiated form of a substance, said method comprising:

a) providing an activated-potentiated form of a substance,
b) assuring absence of molecular form of the said substance in said activated-potentiated form,
c) providing a molecular form of said substance,
d) measuring at least one physical, chemical or biological parameter (A) of said molecular form of said substance using a suitable analytical method,
e) treating said molecular form of said substance with said activated-potentiated form of said substance, and
f) measuring said at least one physical, chemical or biological parameter ($A_M$) of said treated molecular form of said substance using said analytical method,
wherein said activity of said activated-potentiated form of said substance is the degree of difference between A and $A_M$,
wherein the method further comprises of expressing said activity of said activated-potentiated form of said substance in relative units (X) in accordance with the formula $X=C|A-A_M|/A$;
wherein X is a number of activity units
  C is a characteristic parameter that depends on the analytical method used; reflecting an initial physical, chemical and/or biological property of the therapeutic substance,
  A is a characteristic parameter of the therapeutic substance prior to its interaction with the said activated-potentiated form,
  $A_M$ is a value of the same characteristic parameter of the therapeutic substance after its interaction with the said active-potentiated form;
and wherein the analytical method if selected from one of High Performance Liquid Chromatography, Enzyme Immune Assay Analysis, Nuclear Magnetic Resonance.

2. The method of claim 1, further comprising i) treating a molecular form of a different substance with said activated-potentiated form of the first substance, ii) measuring said at least one physical, chemical or biological parameter (B) of said molecular form of said different substance said analytical method, iii) measuring said at least one physical, chemical or biological parameter ($B_M$) of said treated molecular form of said different substance using said analytical method to determine specificity of said method, wherein said method is considered specific when said at least one physical, chemical or biological parameter changes in statistically significant manner for $A-A_M$ and does not change in statistically significant manner for $B-B_M$.

3. The method of claim 1, wherein said step of assuring absence of molecular form of the substance comprises removing the molecular form of said substance.

4. The method of claim 1, wherein said substance is an antibody.

5. The method of claim 4, wherein said antibody is a polyclonal antibody.

6. The method of claim 1, wherein said substance is a small organic molecule.

7. The method of claim 1, wherein said activated-potentiated form is a liquid.

8. The method of claim 1, wherein said activated-potentiated form is impregnated onto a solid carrier.

* * * * *